(12) United States Patent
Purcell et al.

(10) Patent No.: US 8,834,540 B2
(45) Date of Patent: Sep. 16, 2014

(54) POLYAXIAL BONE SCREW WITH LATERAL CONNECTOR

(75) Inventors: Thomas Purcell, Del Mar, CA (US); Darren Reimers, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 13/277,439

(22) Filed: Oct. 20, 2011

(65) Prior Publication Data

US 2012/0101533 A1 Apr. 26, 2012

Related U.S. Application Data

(60) Provisional application No. 61/394,865, filed on Oct. 20, 2010, provisional application No. 61/411,303, filed on Nov. 8, 2010.

(51) Int. Cl.
| | |
|---|---|
| *A61B 17/04* | (2006.01) |
| *A61B 17/86* | (2006.01) |
| *A61F 2/08* | (2006.01) |
| *A61B 17/70* | (2006.01) |

(52) U.S. Cl.
CPC ......... *A61B 17/7043* (2013.01); *A61B 17/7055* (2013.01); *A61B 17/7032* (2013.01); *A61B 17/7037* (2013.01)
USPC ........... 606/305; 606/300; 606/301; 606/264; 606/265

(58) Field of Classification Search
USPC .......................... 606/246, 264–279, 300–321
See application file for complete search history.

(56) References Cited

U.S. PATENT DOCUMENTS

| | | | | |
|---|---|---|---|---|
| 7,892,260 | B2 * | 2/2011 | Mahoney et al. | 606/265 |
| 8,083,777 | B2 * | 12/2011 | Butters et al. | 606/267 |
| 2007/0135817 | A1 | 6/2007 | Ensign | |
| 2008/0125816 | A1 | 5/2008 | Jackson | |
| 2008/0215095 | A1 * | 9/2008 | Biedermann et al. | 606/246 |
| 2008/0243189 | A1 | 10/2008 | Purcell et al. | |
| 2008/0269810 | A1 * | 10/2008 | Zhang et al. | 606/305 |
| 2010/0036420 | A1 * | 2/2010 | Kalfas et al. | 606/250 |
| 2010/0037098 | A1 | 4/2010 | Synthes et al. | |
| 2011/0270325 | A1 * | 11/2011 | Keyer et al. | 606/305 |
| 2012/0071926 | A1 * | 3/2012 | Jani et al. | 606/250 |

* cited by examiner

*Primary Examiner* — Pedro Philogene
*Assistant Examiner* — Christina Negrellirodrigue
(74) *Attorney, Agent, or Firm* — Michael J. Loi

(57) ABSTRACT

A polyaxial screw body includes a side wall defining a lumen having a first end and a second end. An opening disposed at the first end of the lumen, includes an interior surface disposed in the side wall thereabout. The interior surface is adapted to accommodate a head portion of a pedicle screw. A transverse channel extends from a first aperture through the side wall to a second aperture and is adapted to accommodate a portion of a fixation rod therebetween. A lateral connector extending integrally from the side wall.

1 Claim, 8 Drawing Sheets

POLYAXIAL BONE SCREW WITH LATERAL CONNECTOR

CROSS-REFERENCE TO RELATED APPLICATIONS

This application claims priority to U.S. Provisional Patent Application No. 61/394,865, filed Oct. 20, 2010 and U.S. Provisional Patent Application No. 61/411,303, filed Nov. 8, 2010, which are incorporated herein by reference.

FIELD

The present invention relates generally to an apparatus for internal fixation of the spine and, more specifically relates to a polyaxial screw body including a lateral connector integral with the screw body and useful for connecting the screw body to other components of a pelvic fixation device.

BACKGROUND

Certain spinal conditions, including a fracture of a vertebra and a herniated disc, indicate treatment by spinal immobilization. Several methods of spinal joint immobilization are known, including surgical fusion and the attachment of pins and bone plates to the affected vertebras. One known device is a bone interface anchor inserted into at least two spaced-apart vertebras, with a stabilization rod interconnecting the two or more anchors to stabilize the vertebras spanned by the anchors.

During surgical implantation of these prior art stabilization systems, the surgical site is crowded with tissue masses, sponges, and other surgical implements that obstruct access to the anchors. A challenge with current polyaxial screw systems is that lateral connectors typically provide fixation between stabilization rods and a pelvic screw in a spinal construct. However, at the S1-L5 junction, it can be exceedingly difficult or impossible to attach an S1 pedicle screw, L5 pedicle screw, and a lateral connector to a stabilization rod due to special limitations present at the S1-L5 junction. It has been demonstrated that the integrity of the spinal construct is decreased if either the S1 or the L5 pedicle screw is not used. The present invention combines a polyaxial screw body with a lateral connector in a single device that ensures that all necessary fixation points can be achieved in a spinal construct at the S1-L5 junction.

For example, referring to FIG. 5, a portion of a human skeleton illustrates the Sacroiliac region and the L1-L5 and S1 vertebrae. Polyaxial pedicle screws 100 are shown attached to the pedicles of the L2-L4 vertebrae, polyaxial pedicle screws 102 are shown attached to the Sacrum, and polyaxial pedicle screws 104 are shown attached to the Ilium. A conventional polyaxial pedicle screw 106 is attached to one pedicle of the L5 vertebra. Stabilization rods 110a and 110b are illustrated vertically connecting the pedicle screws 100 and 102 on either side of the vertebrae. Ideally, the polyaxial pedicle screw 104 would be attached to the stabilization rod 110a via a lateral connector 112. However, at the S1-L5 junction, the polyaxial pedicle screw 106 may interfere with such connection, as indicated by arrow 114 in FIG. 5, thus making such connection problematic.

Thus, the present invention helps to alleviate a lack of space at the S1-L5 junction as compared to the prior art, allowing the surgeon additional freedom in locating the anchors. The result is a significantly improved polyaxial screw body.

SUMMARY

In one aspect of the present invention, a polyaxial screw body includes a side wall defining a lumen having a first end and a second end. An opening disposed at the first end of the lumen, includes an interior surface disposed in the side wall thereabout. The interior surface is adapted to accommodate a head portion of a pedicle screw. A transverse channel extends from a first aperture through the side wall to a second aperture and is adapted to accommodate a portion of a fixation rod therebetween. A lateral connector extending integrally from the side wall.

In other features, the lateral connector includes a hollow portion and is adapted to receive a member of a pelvic fixation device within the hollow portion. The lateral connector is threaded on an internal surface thereof. The lateral connector is threaded on an external surface thereof. The lateral connector is a member of a first sub-group of practically unique orientations that lie in planes generally perpendicular to the transverse channel and generally parallel to a centerline of the lumen. The lateral connector is a member of a second sub-group of practically unique orientations that lie in planes generally coplanar with a centerline of the lumen. The lateral connector is a member of a third sub-group of practically unique orientations that lie in planes that are non-coplanar with a centerline of the lumen and non-perpendicular to the transverse channel. The lateral connector is a member of a curvilinear group of practically unique orientations including curvature in one or more planes. The apertures comprise axially extending slots, wherein each slot is open toward the second end. The slots are smaller at an open end than at a closed end thereof. A locking cap releasably securable within the screw body and adapted to bear against the portion of the fixation rod accommodated by the slots. A bushing disposed within the screw body and adapted to be disposed between the head portion of a pedicle screw and a portion of a fixation rod.

In another aspect of the present invention, a polyaxial screw assembly includes a polyaxial screw with a proximal end with head and a distal end for attachment to a vertebra. A body member is defined by a side wall and including a lumen having a proximal end and a distal end. An opening at the distal end of the body member is configured to receive the head of the polyaxial screw. A transverse channel is formed in the proximal end of the body member configured to accommodate a fixation rod. A lateral connector integral with the body member and extends radially away from the side wall.

In other features, the lateral connector extends from the side wall within a first plane that is parallel to a centerline of the lumen and perpendicular to a plane formed by the centerline of the lumen and a centerline of the channel. The lateral connector extends from the side wall within a second plane parallel to a centerline of the lumen and non-perpendicular to a plane formed by the centerline of the lumen and a center line of the channel. The lateral connector extends from the side wall within a third plane coplanar with a centerline of the lumen. The lateral connector extends from the side wall within a fourth plane that intersects at least one of a centerline of the lumen and a plane formed by the centerline of the lumen and a centerline of the transverse channel. The lateral connector extends from the side wall in a curvilinear fashion within one or more planes. The lateral connector extends from one of a proximal end of the side wall and a distal end of the side wall. The lateral connector extends from one of a first end of the side wall proximate to a first opening of the transverse channel and a second end of the side wall proximate to a second opening of the transverse channel.

The foregoing summary, as well as the following detailed description of the preferred embodiments, will be understood when read in conjunction with the appended drawings.

DETAILED DESCRIPTION

As used herein, the term "longitudinal" refers to a direction oriented generally parallel to an imaginary centerline of a lumen disposed through a body member, as further described herein below. The terms "lateral" and "transverse" refer to being oriented generally in any direction other than parallel to longitudinal.

Figure 5:
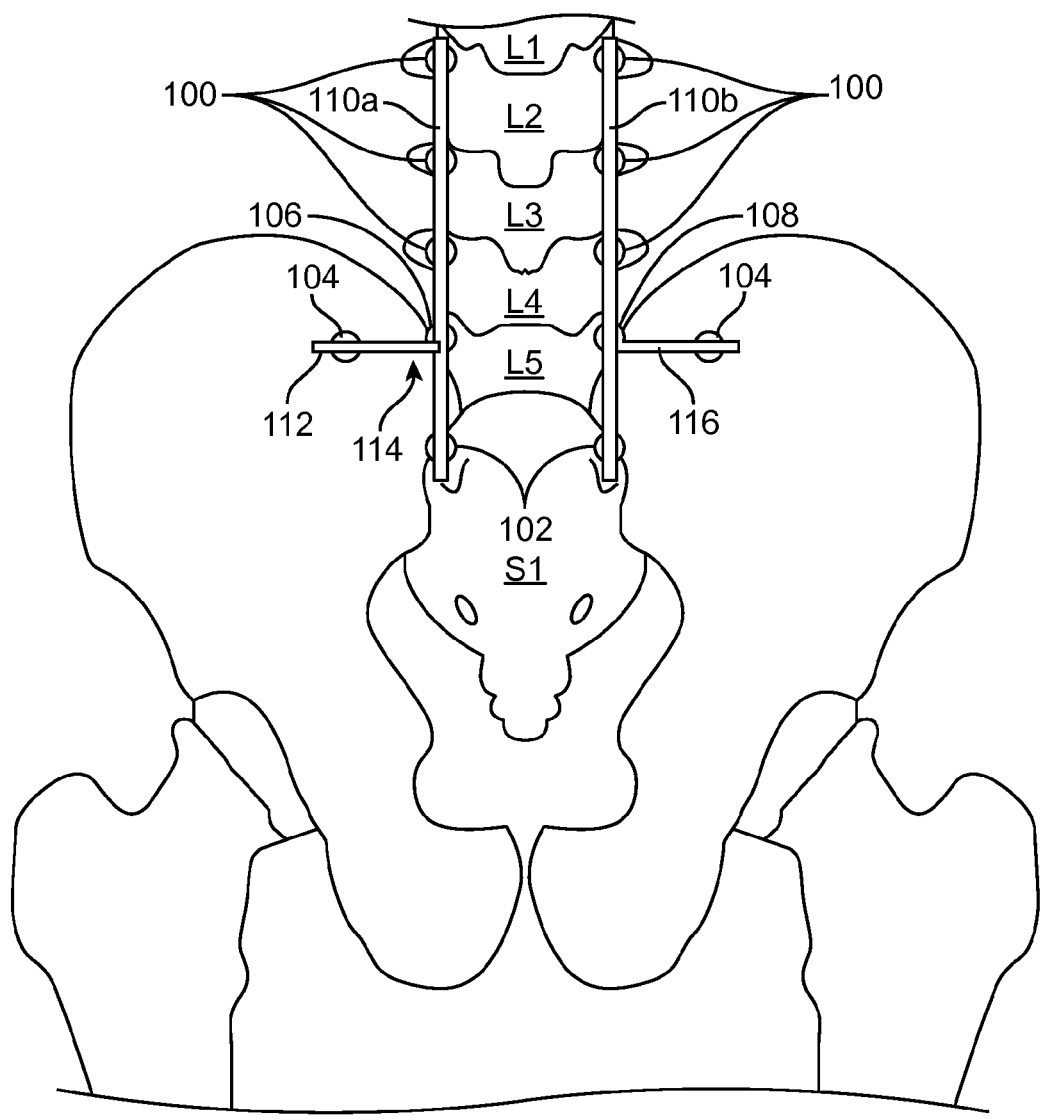
FIG. 5 illustrates a spinal joint immobilization system affixed to a human Sacroiliac region and including a polyaxial pedicle screw of the current invention.

Continuing with FIG. 5, a polyaxial pedicle screw 108 of the current invention is attached to the other pedicle of the L5 vertebra. In contrast to the conventional polyaxial pedicle screw 106, the polyaxial pedicle screw 108 of the current invention includes a lateral connector 116 extending integrally therefrom. The integrally extending lateral connector 116 facilitates a proper connection between the stabilization rod 110b and the polyaxial pedicle screw 104 via the polyaxial pedicle screw 108.

Figure 1A:
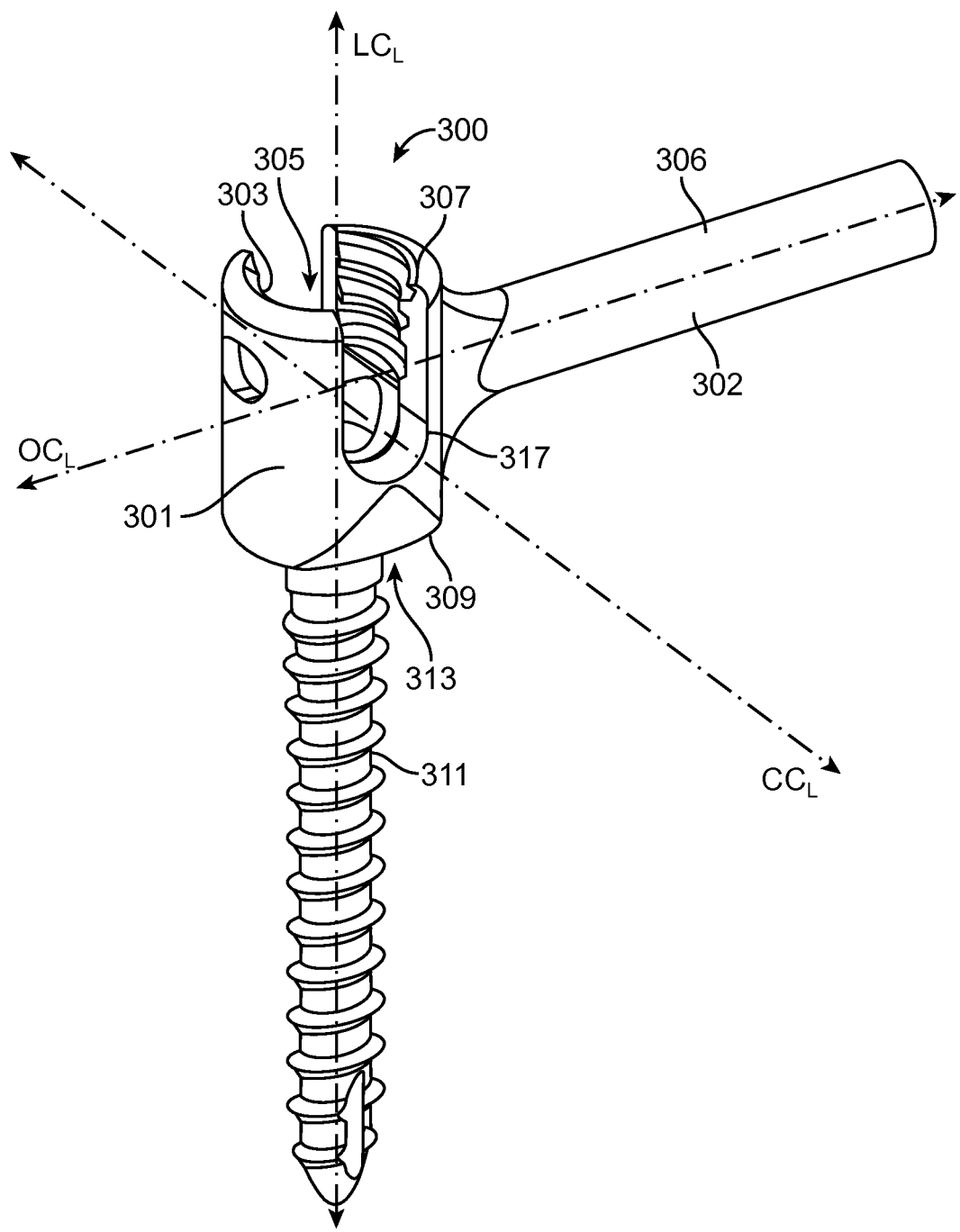
FIG. 1A is a perspective view of an embodiment of a polyaxial screw body.
Figure 1B:
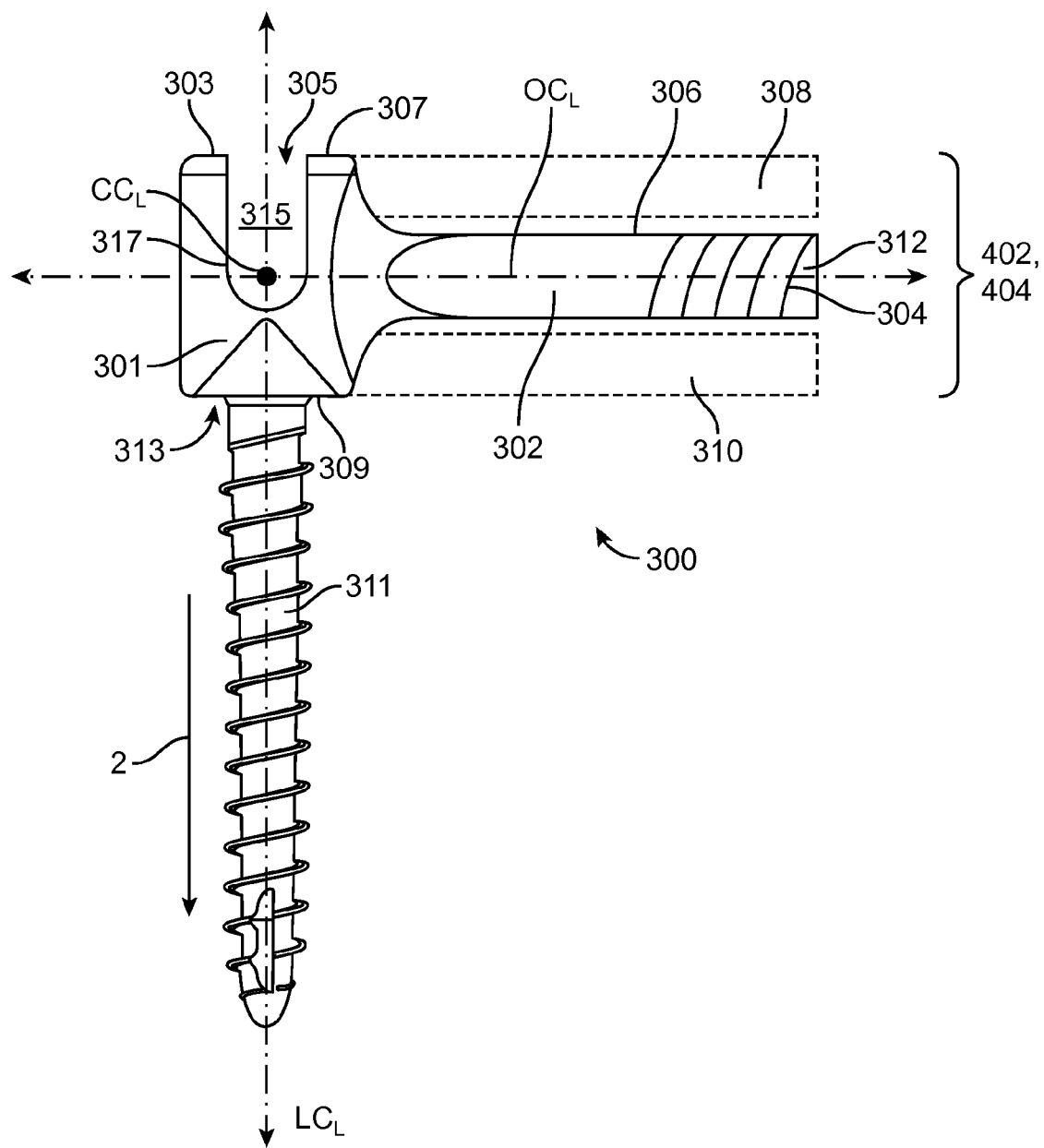
FIG. 1B is an elevational view of the polyaxial screw body of FIG. 1A.

An embodiment of an improved polyaxial screw body 300 comprises a body member 301 and a lateral connector 302 extending integrally from the body member 301, as illustrated in FIGS. 1A and 1B. In one embodiment, the body member 301 includes a side wall 303 that defines a lumen 305 disposed longitudinally through the body member 301 and having first and second ends proximate first and second ends 307, 309 of the body member 301. In this embodiment, a pedicle screw 311 may extend from the lumen 305 through an opening 313 at the second end of the lumen 305. The opening 313 includes an interior surface disposed in the side wall 303 thereabout. The interior surface is adapted to accommodate a head portion of the pedicle screw 311. In one embodiment, the opening 313 includes a curvilinear interior surface disposed in the wall 303 thereabout. The curvilinear interior surface may be adapted to accommodate a head portion, for example, a spherical head portion of a pedicle screw 311. An example of a body member 301 that may be useful in the present invention is disclosed in Purcell et al., U.S. Pat. No. 7,377,923, which is incorporated by reference in its entirety herein.

A channel 315 is defined by a pair of apertures 317, for example, holes or axially extending open ended slots 317 oppositely disposed through the side wall 303. The slots 317 include an open end facing the first end 307 of the body member 301, as illustrated in FIGS. 1A, 1B, 2, 3A, 3B, and 4, such that a fixation rod may be loaded into the slots 317 from the open end and accommodated therebetween. In one embodiment, the slots 317 are smaller at an open end than at a closed end thereof, thereby providing a snap fit and/or inhibiting removal of the fixation rod from the slots 317.

Figure 1C:
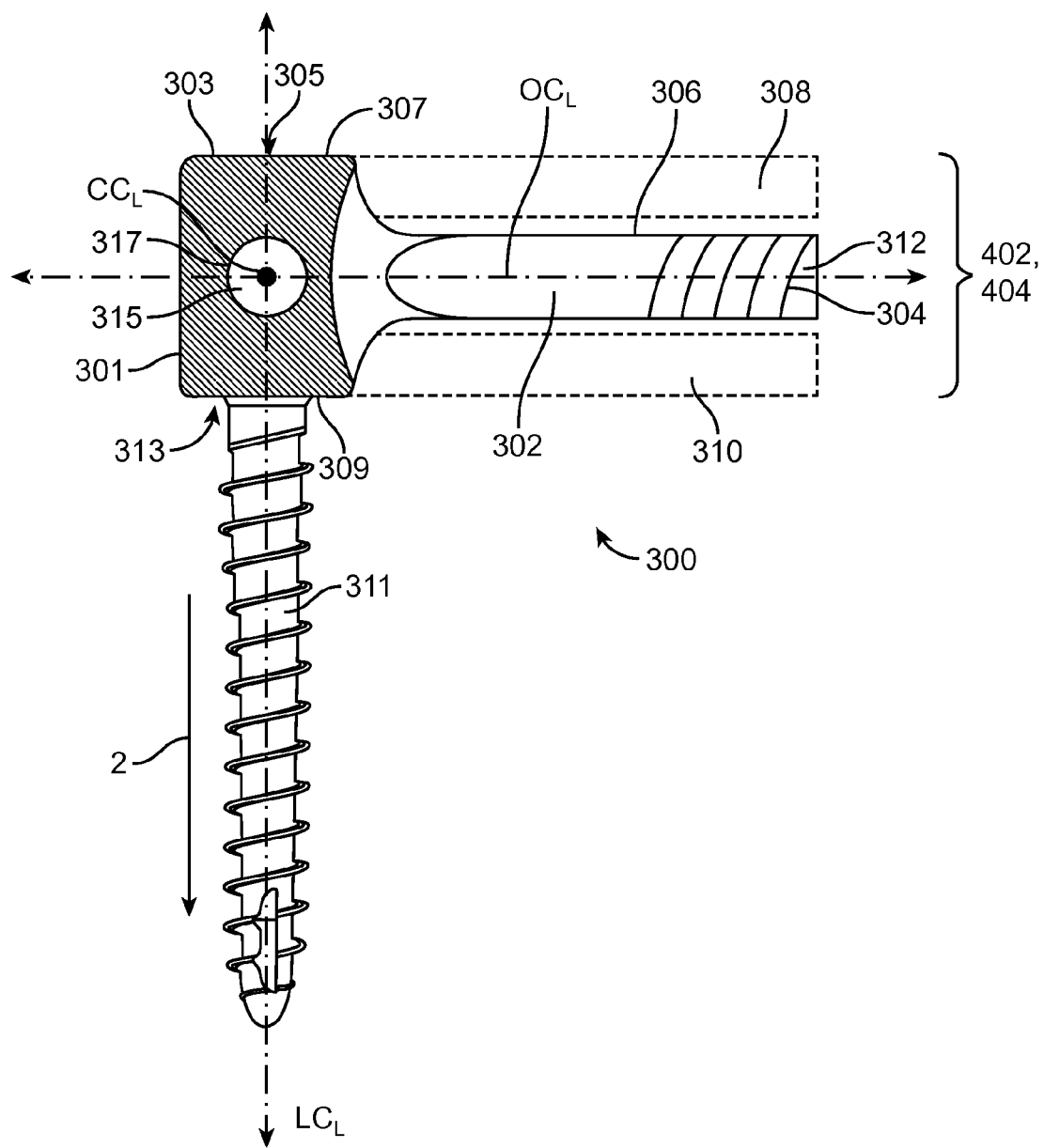
FIG. 1C is an elevational view of another embodiment of a polyaxial screw body.

In another embodiment, the apertures 317 comprise holes 317, as illustrated in FIG. 1C. In this embodiment, a fixation rod is loaded into the hole 317 along the channel 315.

All descriptions herein of relative orientations of the lumen 305 refer to relative orientations of an imaginary centerline $LC_L$ (See FIGS. 1A, 1B, 3A, 3B, and 4) of the lumen 305. Similarly, all descriptions herein of relative orientations of the channel 315 refer to relative orientations of an imaginary centerline $CC_L$ (See FIGS. 1A, 1B, 2, 3B, and 4) disposed through the pair of apertures 317. Further, all descriptions herein of relative orientations of the lateral connector 302 (or any other lateral connectors as described herein below) refer to relative orientations of an imaginary centerline $OC_L$ (See FIGS. 1A, 1B, 3A, and 3B) of the lateral connector 302 (or any other lateral connectors as described herein below). The channel 315 is oriented transverse and generally perpendicular to the lumen 305. The lateral connector 302 may include various orientations relative to the lumen 305 and the channel 315 of the body member 301.

The utility of the polyaxial screw body 300 benefits from a medical professional's ability to select the orientation of the lateral connector 302 relative to the body member 301. Given the crowding of the surgical site, a particular orientation of the lateral connector 302 relative to the body member 301 may be superior to other orientations of the lateral connector 302 relative to the body member 301. Thus, providing the medical professional a choice from a spectrum of orientations not only increases the utility of the screw body 300, but also allows the medical professional to provide optimal care to a patient by selecting the optimum relative orientation of the lateral connector 302.

Figure 2:
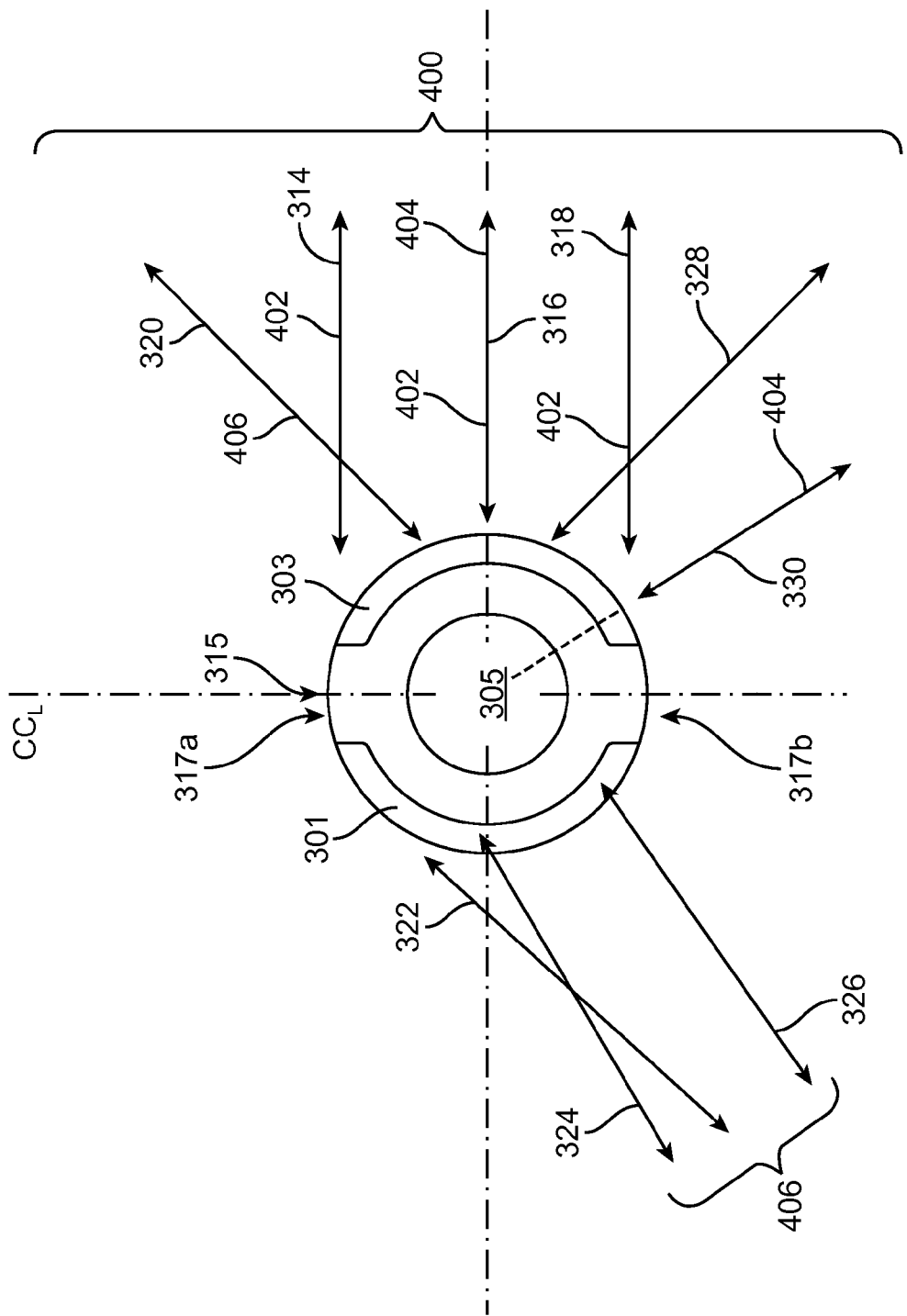
FIG. 2 is an end-on view, taken generally along the line 2 in FIG. 1B, of vertical planes passing through orientations of a lateral connector relative to a body member.

Referring to FIG. 2, the body member 301 is viewed end on from the first end 307. Mathematically, an infinite number of orientations of a line can be encompassed in planes generally parallel to the centerline $LC_L$ of the lumen 305. Each line 314, 316, 318, 320, 322, 324, 326, 328, 330 having arrows at ends thereof in FIG. 2 represents a possible orientation of the line $OC_L$ line relative to the lumen 305. Note that all illustrated orientations of the lines 314, 316, 318, 320, 322, 324, 326, 328, 330 lie in planes generally parallel to the lumen 305. In fact, mathematically, all possible orientations of the line $OC_L$ relative to the lumen 305 necessarily lie in planes generally parallel to the lumen 305. This can be visualized by simply passing a plane coincident with each of the possible orientations perpendicularly into the paper of FIG. 2.

However, because there are limits on tolerances achievable in the manufacture of parts, and because the lateral connector 302 has a finite size, the number of orientations that are practically different from one another in planes generally parallel to the lumen 305 is not infinite. A planar group 400 of orientations can be defined to include all practically unique orientations of the lateral connectors 302 that lie in planes generally parallel to the lumen 305. The planar group 400 includes all the orientations represented by the lines 314, 316, 318, 320, 322, 324, 326, 328, 330 illustrated in FIG. 2.

A first sub-group 402 of the planar group 400 of orientations of the lateral connector 302 includes all practically unique orientations that lie in planes that are generally perpendicular to a plane formed by the centerline $CC_L$ of the transverse channel 315 and the centerline $LC_L$ of the lumen 305 and generally parallel to the lumen 305. Referring to FIG. 2, lines 314, 316, and 318 each represent an example of an orientation of the lateral connector 302 that lies in a plane that is generally perpendicular to the transverse channel 315 and generally parallel to the lumen 305. Thus, the lines 314, 316, and 318 are members of the first sub-group 402.

Referring to FIGS. 1A and 1B, in this embodiment, the lateral connector 302 extends from the side wall 303 in a plane that is generally perpendicular to the transverse channel 315 and generally parallel to the lumen 305. The lateral connector 302 extends in a direction that is generally perpendicular to a plane formed by the centerline $LC_L$ of the lumen 105 and the centerline $CC_L$ of the channel 315. Therefore, in this embodiment, the lateral connector 302 is a member of the first sub-group 402 of the planar group 400 of orientations. The lateral connector 302 is integral with the side wall 304 and is adapted to attach to a member of a pelvic fixation device.

In one embodiment, the lateral connector 302 is partially hollow, whereas in other embodiments the lateral connector 302 is a tubular or solid member. The lateral connector 302 may be threaded on a portion thereof, for example, a distal end thereof, as illustrated in FIG. 1B, or over an entirety thereof as known in the art. Threads 304 may be applied to an exterior surface 306 or an interior surface of the lateral connector 302. The lateral connector 302 may include other connection mechanisms such as, for example, a bayonet socket connection, a spring loaded button and aperture connection, a cotter pin connection, and others as may be known in the art. The lateral connector 302 may have any cross-sectional shape as known in the art, including by way of example and not limitation, circular, elliptical, ovoid, or polygonal including any number of straight line or curvilinear sides.

Referring to FIG. 1B, the lateral connector 302 may extend from the body member 301 from anywhere along a longitudinal extent of the body member 301 from the first end 307 to the second end 309. For example, the lateral connector 302 may extend from the body member 301 proximate the first end 307 or proximate the second end 309, as illustrated by the dashed lines 308, 310, respectively in FIG. 1B, or anywhere in between the first and second ends 307, 309, as illustrated, for example, at 312. Each orientation 308, 310, 312 of the lateral member 302 lies in a plane that is generally perpendicular to the transverse channel 315 and generally parallel to the lumen 305, and thus within the first sub-group 402 of orientations.

Figure 3A:
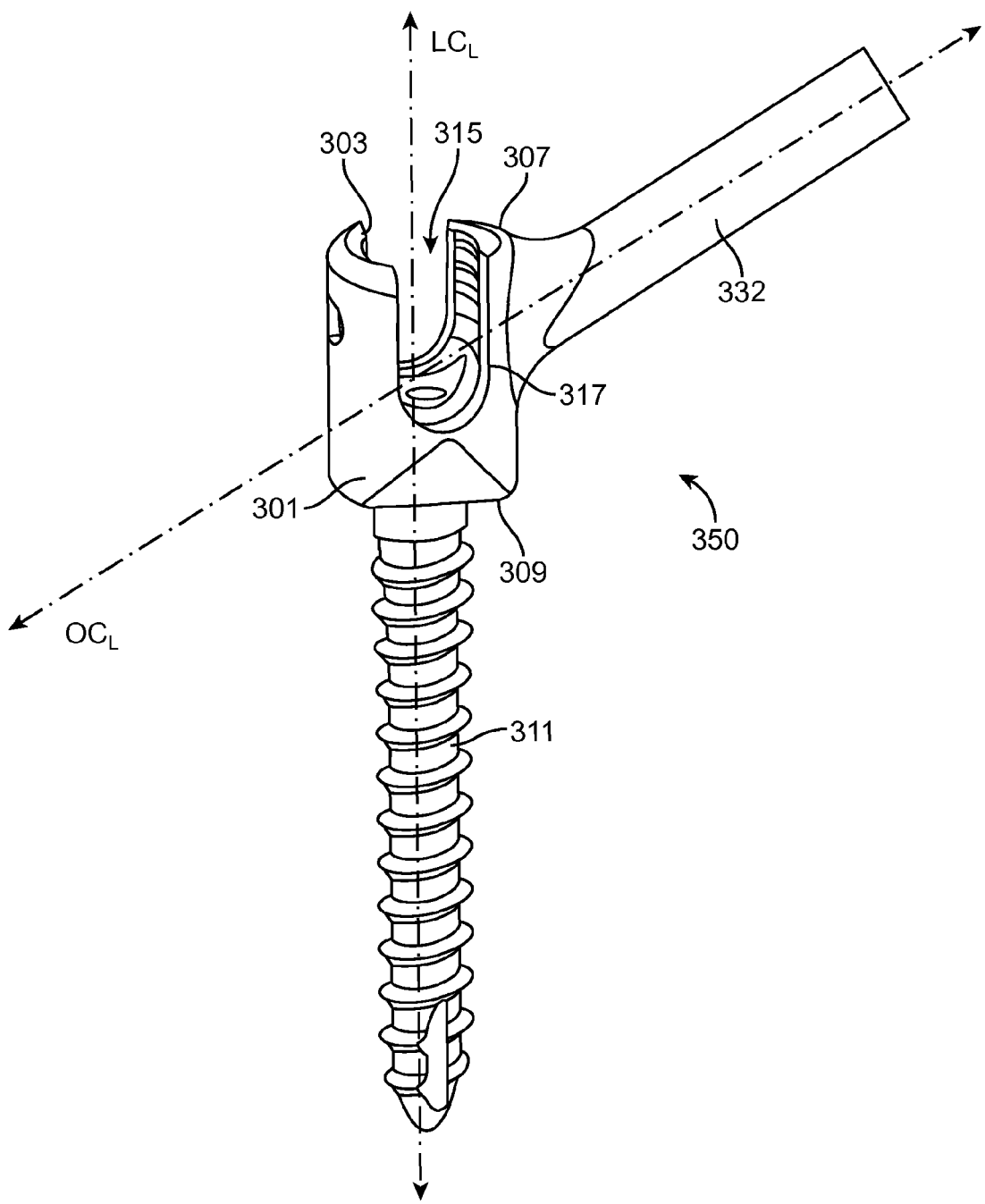
FIG. 3A is a perspective view of another embodiment of a polyaxial screw body.
Figure 3B:
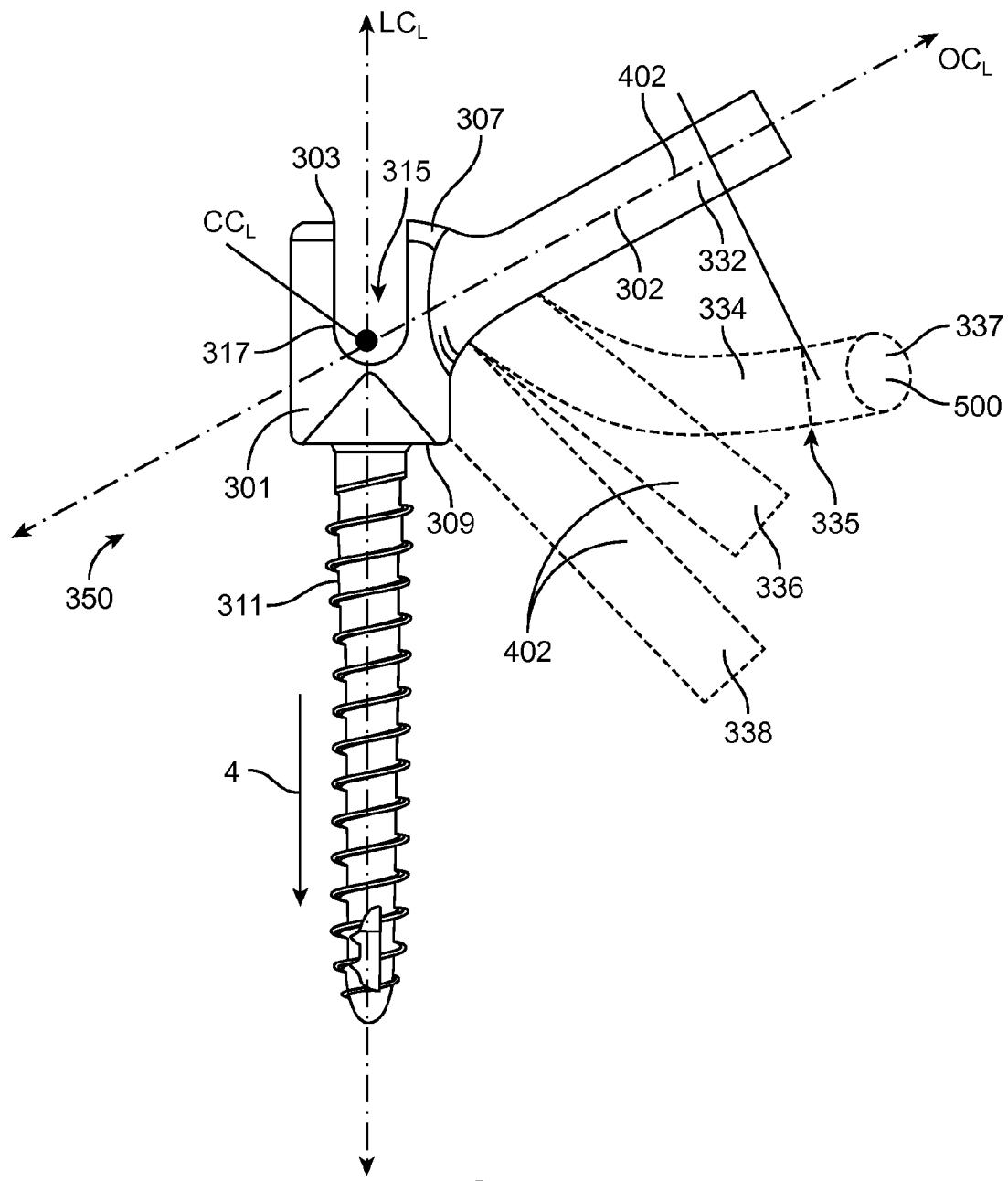
FIG. 3B is an elevational view of the polyaxial screw body of FIG. 3A.

Referring to FIGS. 3A and 3B, in another embodiment of a polyaxial screw body 350, a lateral connector 302 extends from the side wall 303 in an orientation 332 in a plane that is generally perpendicular to the transverse channel 315 and generally parallel to the lumen 305. In this orientation 332, the lateral connector 302 extends away from the body member 301 generally towards the first end 307. The lateral connector 332 may extend from the polyaxial screw body 350 in a direction relatively toward the first end 307 or relatively toward the second end 309 from anywhere along the length of the body member 301 from the first end 307 to the second end 309, as illustrated by the dashed lines 336, 338 in FIG. 3B. Therefore, each orientation 332, 336, and 338 of the lateral connector 302 lies in a plane that is generally perpendicular to the transverse channel 315 and generally parallel to the lumen 305, and thus within the first sub-group 402 of orientations. Further, the first sub-group 402 of orientations includes lateral connectors 302 that extend from the body member 301 from proximate a first end 317a of the channel 315, proximate a second end 317b of the channel 315, or anywhere in between the first and second ends of the channel 315, as represented by the lines 314, 318, and 316, respectively, as shown in FIG. 2.

Referring to FIG. 3B, the lateral connector 302 is illustrated by dashed lines 334 as having a curvilinear orientation in at least one plane. For example, if the orientation 334 was curved in only the plane of the paper (including a distal end 335, as illustrated in FIG. 3B), the orientation 334 would lie entirely in a plane that is generally perpendicular to the transverse channel 315 and generally parallel to the lumen 305, thus making the orientation 334 a member of the first sub-group 402.

However, if the orientation 334 includes a curve into or out of the plane of the paper (including a distal end 337, as illustrated in FIG. 3B), the orientation 334 would lie in more than a single plane and would therefore belong to a group of practically unique orientations that is external to the planar group 400, which we shall call the curvilinear group 500. Each member of the curvilinear group 500 may extend from the body member 301 from any position relative to the transverse channel 315, for example, as illustrated by lines 314, 316, and 318 of FIG. 2, or any position along a longitudinal extent of the body member 301 from the first end 307 to the second end 309 (See FIGS. 1B and 3B).

Referring to FIG. 2, a second sub-group 404 of the planar group 400 of orientations of the lateral connector 302 includes those that are generally co-planar with the lumen 305, but not necessarily generally perpendicular to the transverse channel 315. The lines 316 and 330 lie in planes that include the lumen 305, thus, the lines 316 and 330 represent orientations that are part of the second sub-group 404. Referring to FIGS. 1B and 2, note that orientations represented by the dashed lines 308 and 310, and the lines 312 and 316 are members of both the first sub-group 402 and the second sub-group 404. The remaining lines, 320, 322, 324, 326, and 328 illustrated in FIG. 2 lie in planes that are neither generally co-planar with the lumen 305 nor generally perpendicular to the transverse channel 315, and thus represent orientations that are members of a third sub-group 406 of the planar group 400.

Figure 4:
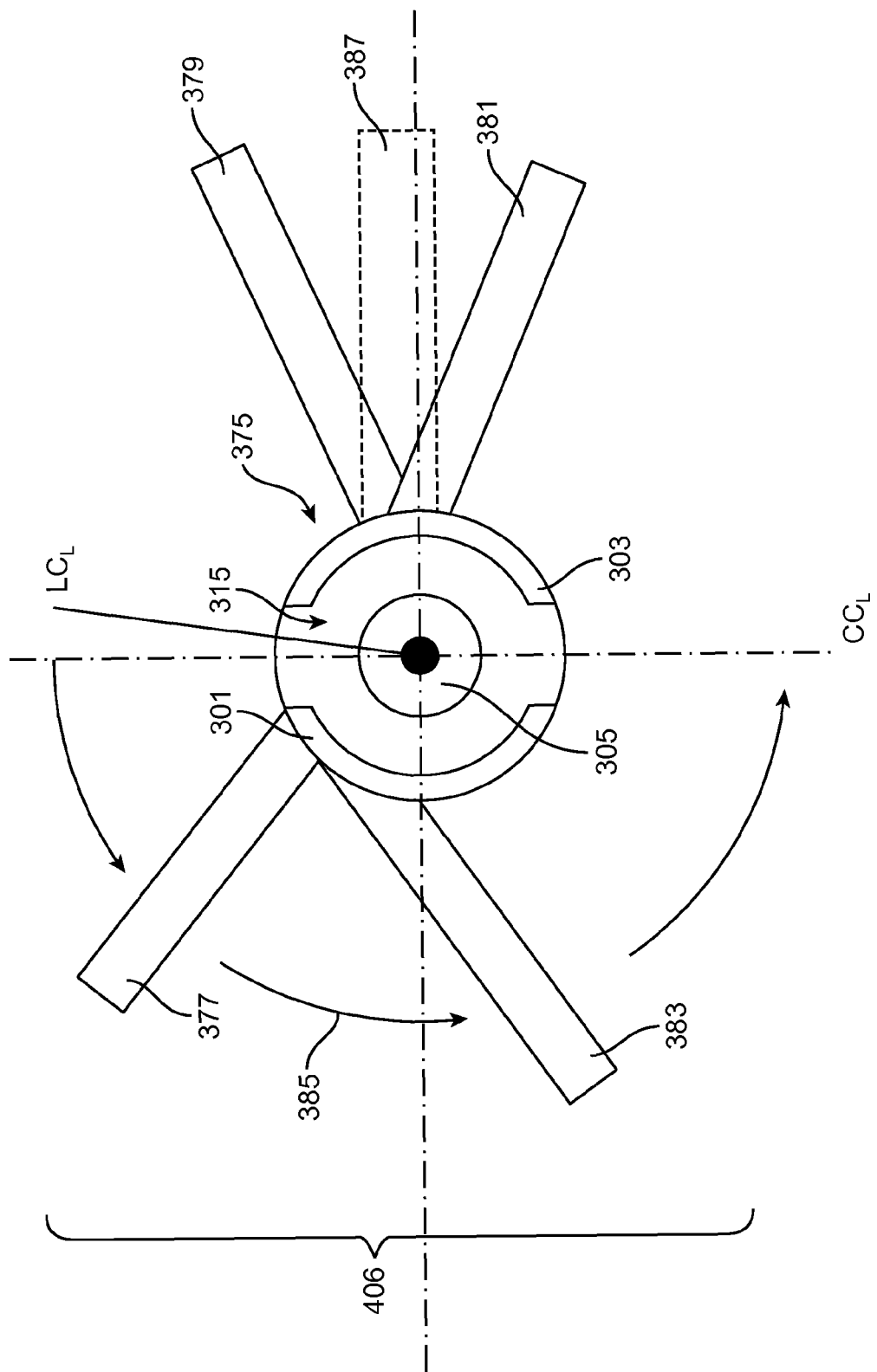
FIG. 4 is an end-on view, taken generally along the line 4 in FIG. 3B, of orientations of a lateral connector relative to a body member.

Referring to FIG. 4, another embodiment of a polyaxial screw body 375 includes a lateral member, such as for example, any of the lateral members 377, 379, 381, or 383. Each of the lateral members 377, 379, 381, or 383 may extend from the body member 301 from any position relative to the transverse channel 315, for example, as illustrated by lines 314, 316, and 318 of FIG. 2, or any position along a longitudinal extent of the body member 301 from the first end 307 to the second end 309 (See FIGS. 2B and 3B). Further, as illustrated by curved line 385, the lateral members 377, 379, 381, 383 may have any rotational orientation relative to the transverse channel 315.

The lateral members 377, 379, 381, 383 may extend from the body member 301 at any angle relative to the lumen 305. The lateral connectors 377, 379, 381, 381, are part of the third sub-group 406 of practically unique orientations including members that lie in a plane generally parallel to the lumen 305, but are not generally co-planar with the lumen 305 or generally perpendicular to the transverse channel 315. Note that orientation 387 represented by dashed lines is not a member of the third sub-group 406, but is a member of the first sub-group 402 and the second sub-group 404.

The groups of practically unique orientations presented hereinabove provide a convenient way to classify all of the possible practically unique orientations of the lateral connector 302 relative to the body member 301. A global group comprising of all orientations would include the curvilinear group 500 and the planar group 400 as sub-groups thereof. The planar group 400 includes the first, second, and third sub-groups 402, 404, 406, as defined hereinabove. Note that there are practically unique orientations that are members of both the first and second sub-groups 402 and 404.

The lateral connectors 302 may integrally extend from the body member 301 in any of the practically unique orientations described hereinabove and the polyaxial screw bodies 300, 350, 375 may be manufactured from methods as known in the art, including by way of example and not limitation, casting, machining, or combinations of casting and machining. Material for the polyaxial screw bodies 300, 350, 375 may be a suitable material as known in the art, including by way of example and not limitation stainless steel, Nitinol or titanium, stainless steel, other shape memory metal materials, other metals, plastic, synthetic material, other suitable materials, or any combination thereof. Because the sub-groups 402, 404, 406, and the curvilinear group 500 defined hereinabove refer to groups of practically unique orientations and not groups of mathematically possible orientations, each of the sub-groups 402, 404, 406, and the curvilinear group 500 does not include an infinite number of members. Rather, because the number of practically unique orientations is limited by the finite size and shape of the body member 301 and the lateral member 302 and the tolerances of modern manufacturing techniques, each of the sub-groups 402, 404, 406, and the curvilinear group 500 includes a finite, albeit large, number of members.

An improved polyaxial screw body is presented. A lateral connector integrally extends from a body member of the polyaxial screw body to utilize less space than a conventional polyaxial screw body utilizing a conventional fixation rod connector. The lateral connector may integrally extend from the body member in any orientation as desired to provide a medical professional a choice in selection of the optimum orientation.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the polyaxial screw body described herein and to teach the best mode of carrying out the same.

The invention claimed is:

1. A sacral to lumbar fixation system comprising:
 a polyaxial screw including
  a proximal end with a first head and a distal end for attachment to a vertebra;
  a first body member defined by a side wall and including a lumen having a proximal end and a distal end;
  a first opening at the distal end of the first body member that receives the first head of the polyaxial screw;
  a first transverse channel formed in the proximal end of the first body member extending from a first aperture in the side wall to a second aperture in the side wall and that receives a fixation rod; and
  a lateral connector including a tubular shape integral with the first body member and extending radially away from the side wall at an angle relative to the first transverse channel; and
 a pelvic fixation device including
  a proximal end with a second head and a distal end for attachment to a sacrum;
  a second body member defined by a side wall and including a lumen having a proximal end and a distal end;
  a second opening at the distal end of the second body member that receives the second head of the pelvic fixation device; and
  a second transverse channel formed in the proximal end of the second body member extending from a first aperture in the side wall to a second aperture in the side wall that receives the lateral connector.

* * * * *